(12) United States Patent
Sasayama

(10) Patent No.: US 7,508,907 B2
(45) Date of Patent: Mar. 24, 2009

(54) X-RAY ANALYSIS APPARATUS

(75) Inventor: Norio Sasayama, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 11/845,540

(22) Filed: Aug. 27, 2007

(65) Prior Publication Data

US 2008/0056442 A1    Mar. 6, 2008

(30) Foreign Application Priority Data

Aug. 29, 2006    (JP)    ............................. 2006-232192

(51) Int. Cl.
  *G01N 23/223*    (2006.01)
  *G21K 1/02*    (2006.01)
(52) U.S. Cl. ......................................... 378/45; 378/149
(58) Field of Classification Search .................... 378/44, 378/45, 70, 83–90, 145, 147–153
See application file for complete search history.

(56) References Cited

U.S. PATENT DOCUMENTS 5,937,026 A  *  8/1999  Satoh ........................... 378/44

OTHER PUBLICATIONS

A. Bjeoumikhov et. al., "New generation of polycapillary lenses: manufacture and applications" X-ray Spectrom., 2003, 32, p. 172-178.

* cited by examiner

*Primary Examiner*—Irakli Kiknadze
(74) *Attorney, Agent, or Firm*—Brinks Hofer Gilson & Lione

(57) ABSTRACT

When an X-ray focused by using an X-ray lens is irradiated to a sample, there is generated an X-ray halo component at the peripheral part of the focal point of the focused X-ray in the sample and, by this, precision of an analysis of a microscopic region becomes an issue. In order to control the shape of the X-rays from the X-ray lens, a collimator is installed between the X-ray lens and the sample, with an opening part having a tapering shape in which the opening at the side toward the sample is made smaller than that at the side toward the X-ray lens.

15 Claims, 4 Drawing Sheets

X-RAY ANALYSIS APPARATUS

This application claims priority under 35 U.S.C. § 119 to Japanese Patent Application No. JP2006-232192 filed Aug. 29, 2006, the entire content of which is hereby incorporated by reference.

BACKGROUND OF THE INVENTION

1. Field of the Invention

The present invention relates to an X-ray analysis apparatus in which, by irradiating an X-ray to a sample and detecting a ray or a light radiating from the sample, such as X-ray and electrons, there is performed an element analysis or a composition analysis of the sample from that radiant ray. Especially, it relates to an X-ray analysis apparatus possessing an X-ray lens and a collimator.

2. Description of the Related Arts

For some time, as a method of performing the element analysis or the composition analysis of the sample, there is known a method of analyzing by irradiating the X-ray to the sample being examined from an X-ray tubular bulb, and detecting a fluorescent X-ray which is generated by an element contained in the sample which is excited by the irradiating X-ray, or the like by a detection system. Especially, there is a fluorescent X-ray analysis apparatus capable of specifying a contained amount of an object element by detecting the intensity of the fluorescent X-ray relating to the desired object element from a spectrum of the fluorescent X-ray.

Further, in the fluorescent X-ray analysis apparatus that is a conventional X-ray analysis apparatus, in the case of analyzing a microscopic region, the collimator having an opening of a size similar to the analyzed region is installed between the X-ray tubular bulb and the sample, and the microscopic part is analyzed by utilizing the X-rays passing through the opening. However, since most of the X-rays emitted from the X-ray tubular bulb are intercepted by the collimator, an intensity of the irradiated X-ray decreases, so that the X-ray analysis detection efficiency is bad.

Whereupon, in order to make the efficiency good, there is known a method of irradiating the microscopic region by focusing the irradiating X-rays, which previously were intercepted, by utilizing an X-ray lens such as polycapillary. (For example, refer to A. Bjeoumikhov et. al., "New generation of polycapillary lenses: manufacture and applications" X-ray Spectrom., 2003, 32, P. 172-178.)

FIG. 4 is a schematic view showing a constitution of the X-ray analysis apparatus by the prior art. It is constituted by an X-ray tubular bulb 1 generating the X-ray, the polycapillary used as an X-ray lens 2 focusing the X-ray, a sample S to be measured, and an energy dispersion type X-ray detector used as a detector 5 detecting the fluorescent X-ray.

The X-ray emitted from the X-ray tubular bulb 1 is focused onto the sample S by the X-ray lens 2, thereby exciting a constituent element in the sample S. The fluorescent X-ray emitted from the excited constituent element is measured in its energy by the detector 5 and, from the spectrum obtained by accumulating the measurement values, there is found the concentration of the constituent element in the sample S, or the thickness of a thin film on the sample surface.

Incidentally, although the conventional example shown in FIG. 4 is the fluorescent X-ray analysis apparatus, also in other X-ray analysis apparatuses having a mechanism measuring a phenomenon such as electrons, diffracted X-ray, or light which is generated by excitation with irradiating X-rays as the excitation source, it is known that the X-ray lens is similarly used for analysis of a microscopic part.

The X-ray lens is a device focusing the X-ray by utilizing a reflection, a scattering, an absorption or the like of the X-ray in the lens. However, in the case of X-rays of a high energy, efficiency of the reflection, the scattering or the absorption is low, and a probability of irradiating a portion other than a focal point on the sample due to deviation from a focused light path becomes high. In other words, in a method using the X-ray lens, focusing efficiency of the high energy X-ray is low, and there is increase in a halo component (distribution spread at the sample surface) faintly irradiating a focal point periphery and so out of focus. As a result, in a case where an excited X-ray of the high energy is necessary, it becomes impossible to neglect influence due to exciting simultaneously a region spreading to the focal point periphery, and accuracy as to which portion is being measured in an X-ray analysis is lost, so that a measurement precision becomes an issue.

Further, in the X-ray analysis, if a primary filter changing the energy distribution of the excited X-rays is used for the purpose of a microanalysis or the like, there is an issue that an influence of the halo component is intensified.

SUMMARY OF THE INVENTION

The present invention is one made in view of the above-mentioned circumstances, and its object is to provide an X-ray analysis apparatus in which, even in a case where the X-ray of the high energy is irradiated, it is possible to perform a measurement in the sample of the microscopic region by making such that an optimally focused X-ray can be irradiated by suppressing the influence of the halo in the focal point periphery.

In order to solve the above problem, the present invention provides an X-ray analysis apparatus comprising an X-ray tubular bulb generating an X-ray, an X-ray lens focusing the X-ray and irradiating it to a sample, a collimator provided between the X-ray lens and the sample, and a detector detecting a radiant ray or a light which is emitted from the sample upon the irradiation by the X-ray, wherein an opening part provided in the collimator is such a shape that it is smaller at the side toward the sample than at the side toward the X-ray lens.

The present invention brings about such an advantage as described below.

By the fact that the opening part provided in the collimator is made the shape in which it is smaller at the side toward the sample than at the side toward the X-ray lens, it is possible to reduce the halo component irradiated to the sample and focus the X-rays to irradiate only the microscopic region, and the precision of microscopic region analysis is improved.

DESCRIPTION OF THE PREFERRED EMBODIMENTS

Figure 1:
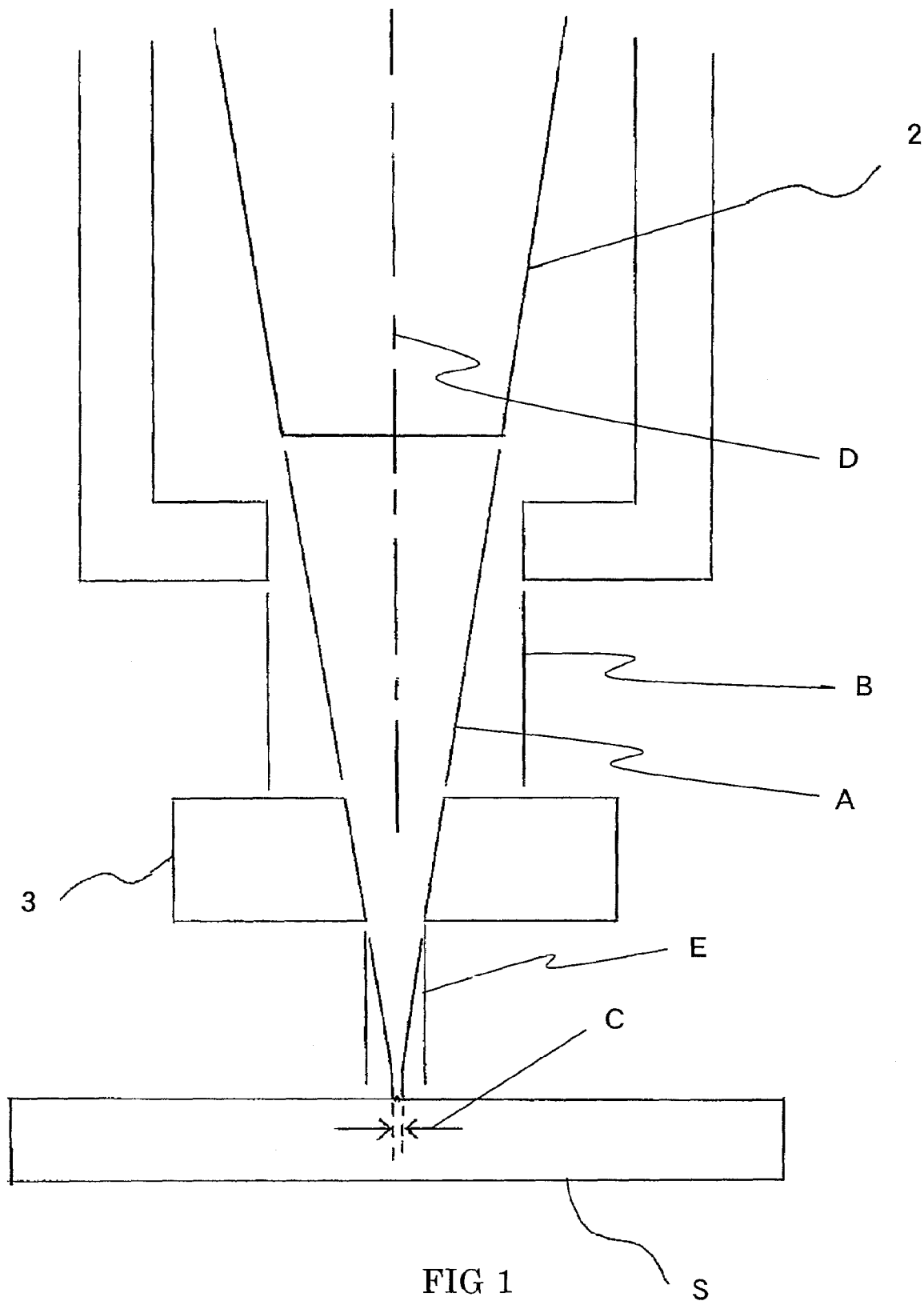
FIG. 1 is a schematic view in which a collimator vicinity of an X-ray analysis apparatus concerned with an embodiment 1 of the present invention is enlarged.

Hereunder, an implementation mode of the present invention is explained about each embodiment by referring to the drawings. However, the following implementation mode is not one limiting the present invention.

Embodiment 1

Figure 3:
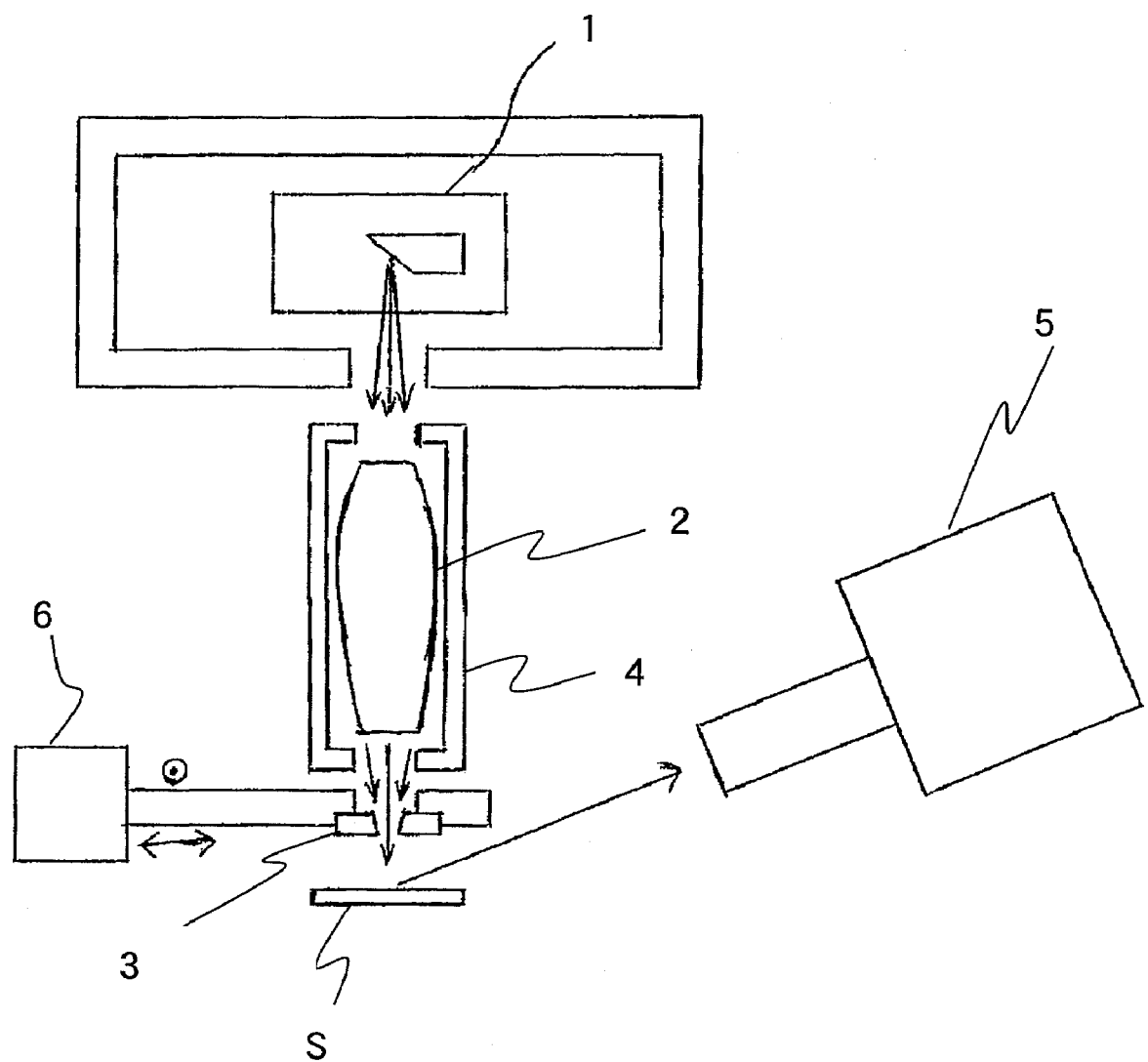
FIG. 3 is a schematic, constitutional view of the X-ray analysis apparatus concerned with the present invention.
Figure 4:
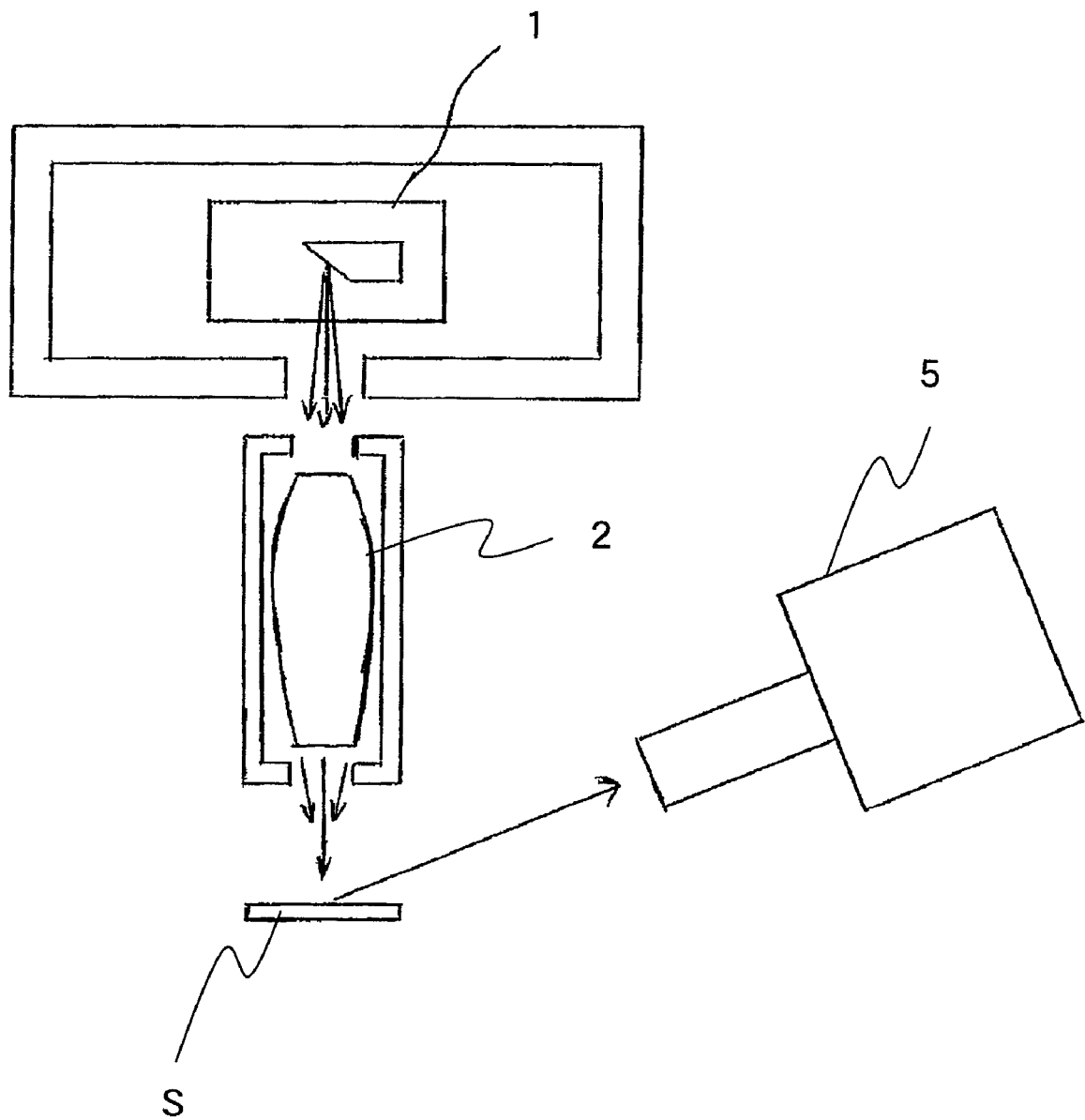
FIG. 4 is a schematic, constitutional view of a conventional X-ray analysis apparatus.

FIG. 3 is a schematic view showing a constitution of an X-ray analysis apparatus by the present invention. It is constituted by an X-ray tubular bulb 1 generating the X-ray, a polycapillary used as the X-ray lens 2 focusing the X-ray, a case 4 provided around this polycapillary 2, which supports the polycapillary and interrupts the X-ray deviating greatly from the polycapillary, a sample S which is the object measured, a energy dispersion type X-ray detector used as the detector 5 detecting the fluorescent X-ray, a tapering collimator 3 which is installed between the X-ray lens and the sample and possesses an opening for controlling a shape of the X-ray from the X-ray lens, and in which the opening at the side toward the sample is made smaller than the opening toward the X-ray lens, and a two-axis drive section for moving a position of the collimator 3 relative to the sample S surface.

The X-ray emitted from the X-ray tubular bulb 1 is focused and irradiated onto the sample S by the X-ray lens 2, thereby exciting constituent elements in the sample S. The fluorescent X-rays emitted from the exited constituent elements are detected by the detector 5, their energy is measured by a pulse height analyzer (not shown in the drawing) or the like and, from the spectrum obtained by accumulating the measurement values, there can be measured the concentrations of the constituent elements in the sample S, or the thickness of the thin film on the sample surface.

In the present embodiment, there is used the X-ray tubular bulb 1 of a maximum voltage 50 KV specification.

In this connection, in the X-ray actually measured, besides the above fluorescent X-ray, there are included also the exciting X-rays scattered by the sample, or the like.

Incidentally, the polycapillary is one constituted by bundled fine tubes comprising fine fibers.

In FIG. 1, there is shown an enlarged view of a peripheral part of the collimator 3 of the X-ray analysis apparatus in FIG. 3.

There are a focused component of the X-ray, which is shown being focused in a focused light path A exiting from a tip of the polycapillary type X-ray lens 2, and a halo component of the X-ray, which is shown in a halo light path B transmitting through the polycapillary type X-ray lens 2 without being focused.

The opening the collimator 3 is made smaller at the side toward the sample S at the side toward the X-ray lens 2 side, a tapered shape so as not to interrupt the focused component of the X-ray. At the same time, in order that the range of paths other than the focused light path A all are interrupted by the collimator and the interrupting efficiency in regard to the halo component becomes maximum, the shape of the opening at the inner wall of the collimator follows a shape of the focused light path A, or approximately coincides with it.

By this, there becomes such that it is possible to reduce the halo component of the X-ray, and irradiate as much as possible the focused X-rays from the X-ray lens to the microscopic part of the sample without being impaired.

Further, as to a material and a shield part thickness of the collimator in the present embodiment, there is used one which is made of tungsten and whose thickness is 1 mm.

Embodiment 2

Figure 2:
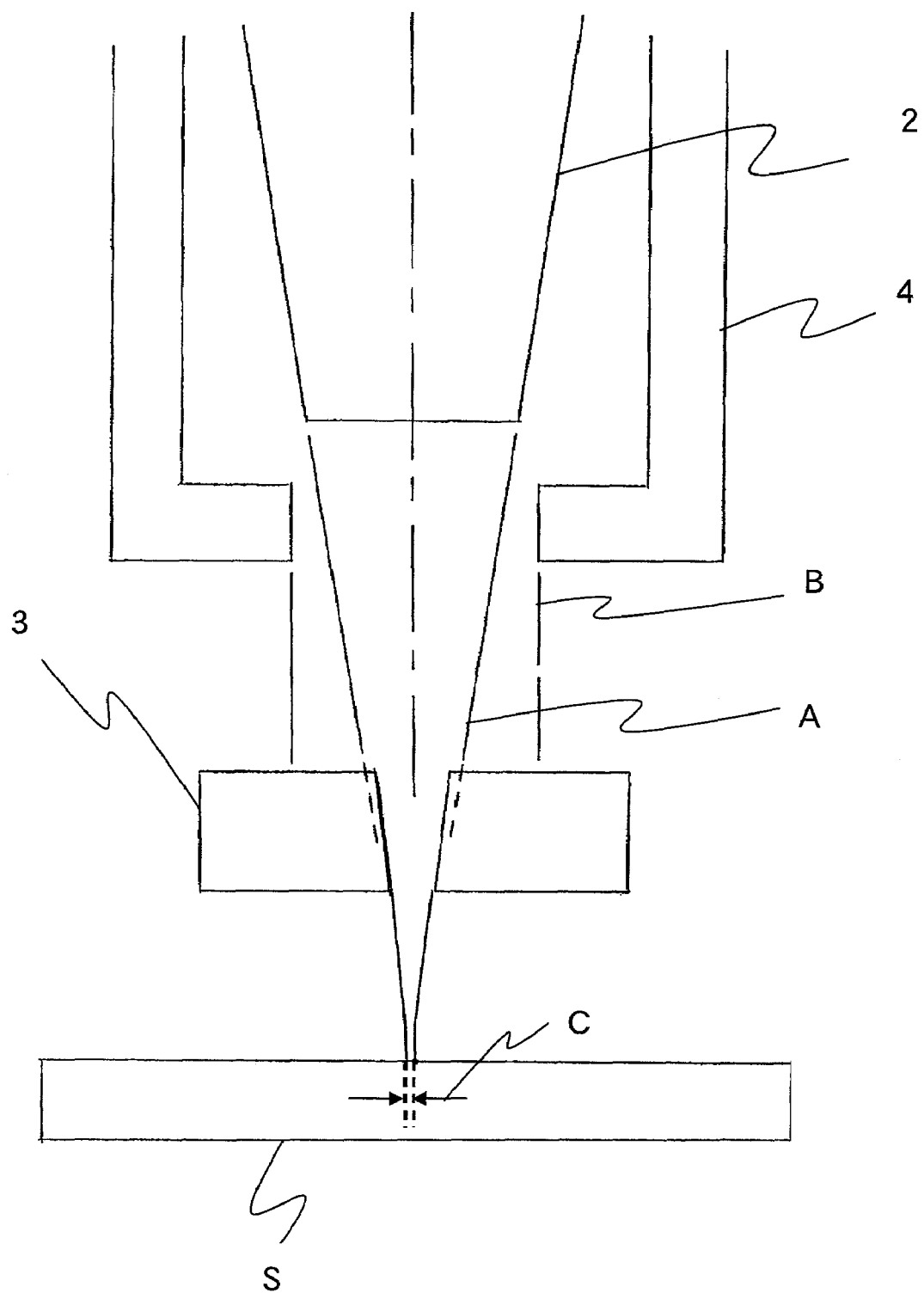
FIG. 2 is a schematic view in which the collimator vicinity of an X-ray analysis apparatus concerned with an embodiment 2 of the present invention is enlarged.

FIG. 2 is a schematic view of the collimator vicinity, which shows an embodiment 2 in the X-ray analysis apparatus by the present invention. Incidentally, since its basic constitution is the same as the embodiment 1, the explanation of a duplicate portion is omitted.

As shown in FIG. 1, in a case where the light path of the entire halo component is shown by the lines B and the halo component passing through the opening part of the collimator 3 is indicated by lines E, the X-ray of the halo component E is irradiated to a portion wider than a diameter of a focal point C of the polycapillary type X-ray lens. The present embodiment is one used in a case where, it is impossible to neglect the slight influence of this phenomenon on the microscopic part analysis.

In the collimator 3 used in the present embodiment, the opening both at side toward the X-ray lens and the side toward the sample are made smaller than the collimator 3 in the embodiment 1.

In order that the portion near an optical axis D of the X-ray lens within the focused component of the focused light path A is not interrupted, and the maximum interruption efficiency of the halo component of the halo light path B is achieved, there is made a collimator shape in which a fixed proportion of the focused light path A is interrupted. Although it follows that one part of the focused component is interrupted, in comparison with FIG. 1 showing the embodiment 1, the opening diameter on the side of the collimator 3 toward the sample S is made smaller, and the collimator made is one in which a reduction in the halo component passing through the opening part of the collimator 3, which is given priority here, is made larger.

In the present embodiment, in comparison with the embodiment 1, both the opening diameter at the side toward the sample and the opening diameter at the side toward the lens are made smaller by 20% than the diameter of the focused light path.

In the present embodiment, since the intensity of the focused component in the focused light path is higher at positions closer to optical axis center of the X-ray lens, the exciting X-ray intensity undergoes a reduction limited to about 8% compared with the embodiment 1 notwithstanding the fact that an opening area on the side toward the sample S is made smaller by about 35% than the embodiment 1.

By this, in comparison with the embodiment 1, although a focused X-ray intensity from the X-ray lens becomes partly weak, since the X-ray can be irradiated to the microscopic part of the sample with the halo component of the X-ray being more reduced, it is possible to perform the microscopic part analysis.

Incidentally, as to the opening part of the collimator in the present embodiment, although circular one is used here, it may be another shape such as a square.

Incidentally, the shape of an inner wall of the opening part of the collimator is not one limited to a shape similar to the focused light path A from the X-ray lens, and the inner wall of the opening may have a concave shape, or in the opening on the side toward the sample may be made still smaller.

Incidentally, in the X-ray analysis apparatus of the present embodiment, although it is an energy dispersion type fluorescent X-ray analysis apparatus in which X-rays are used in the excitation source and there is used a detector, such as semiconductor detector or proportional counter tube, for detecting the fluorescent X-ray generated by that excitation, there may be used a wavelength dispersion type fluorescent X-ray analysis apparatus, or an X-ray analysis apparatus in which there is used a detector for detecting the electrons, diffracted X-ray or the light which are generated by irradiating the X-ray to the sample.

Incidentally, in a case where, in the collimator concerned with the present invention, it is desired to intercept the halo component still more using the same shape, this can be achieved by decreasing the opening diameter at the side toward the sample S and narrowing the spacing between the sample S and the collimator 3. In the present embodiment, the collimator 3 is disposed in a position closer to the sample S side than the X-ray lens 2.

Further, plural collimators whose opening shapes differ can be installed so that they can be switched by using a two-axis drive section 6, so that an optimum collimator for different measurement conditions can be selected.

Further, as the X-ray lens, by using the polycapillary which does not make the X-ray from the X-ray tubular bulb into monochrome, it is possible to utilize the excited X-ray of a wide energy range.

What is claimed is:

1. An X-ray analysis apparatus comprising:
    an X-ray tubular bulb configured to generate an X-ray;
    an X-ray lens having one end which receives the X-ray from the X-ray tubular bulb and another end which emits the focused X-ray onto a sample;
    a collimator provided between said another end of the X-ray lens and the sample at non-zero distances away therefrom, the collimator having an opening formed therethrough which is shaped to have cross-sections substantially equal to or smaller than corresponding cross-sections of the focused X-ray passing through the opening; and
    a detector configured to detect a fluorescent X-ray excited out from the sample by the focused X-ray allowed through the opening of the collimator.

2. An X-ray analysis apparatus according to claim 1, wherein the opening of the collimator is shaped to have the cross-sections substantially equal to the corresponding cross-sections the focused X-rays passing through the opening.

3. An X-ray analysis apparatus according to claim 1, wherein the opening of the collimator is shaped to have the cross-sections smaller than the corresponding cross-sections of the focused X-rays passing through the opening.

4. An X-ray analysis apparatus according to claim 3, wherein the opening is shaped to have the cross-sections each smaller by a constant rate than a corresponding cross-section of the focused X-ray passing through the opening.

5. An X-ray analysis apparatus according to claim 4, wherein the constant rate is about 20%.

6. An X-ray analysis apparatus according to claim 1, wherein the collimator is positioned closer to the sample than to the X-ray lens.

7. An X-ray analysis apparatus according to claim 1, wherein the detector has a function detecting the X-ray.

8. An X-ray analysis apparatus according to claim 1, wherein the X-ray lens is made of a polycapillary.

9. An X-ray analysis apparatus according to claim 1, wherein the opening is shaped to become generally narrower from an X-ray entrance thereof towards an X-ray exit thereof.

10. An X-ray analysis apparatus according to claim 1, wherein the opening has a cross-section of a shape other than a circle.

11. An X-ray analysis apparatus according to claim 1, wherein the opening has a peripheral wall which is concave in shape.

12. An X-ray analysis apparatus according to claim 1, further comprising at least one other collimator having an opening of a shape different from that of the opening of the collimator.

13. An X-ray analysis apparatus according to claim 1, wherein the collimator has a thickness of about 1 mm.

14. An X-ray analysis apparatus according to claim 1, wherein the X-ray tubular bulb generates the X-ray at a maximum energy of 50 KV sufficiently strong to emit an innegligible amount of halo X-ray onto the sample without the collimator.

15. An X-ray analysis apparatus according to claim 1, further comprising a case surrounding the X-ray lens configured to block halo X-ray from the X-ray lens.

* * * * *